United States Patent
Jackson et al.

[11] Patent Number: 5,318,038
[45] Date of Patent: Jun. 7, 1994

[54] INFANT RESPIRATORY IMPEDANCE MEASURING APPARATUS AND METHODS USING FORCED OSCILLATIONS

[75] Inventors: Andrew C. Jackson, Brookline; Kenneth R. Lutchen, Framingham, both of Mass.

[73] Assignee: Trustees of Boston University, Boston, Mass.

[21] Appl. No.: 5,835

[22] Filed: Jan. 19, 1993

[51] Int. Cl.$^5$ ............................................. A61B 5/085
[52] U.S. Cl. ................................... 128/720; 128/716
[58] Field of Search ................. 128/716, 720, 724–730

[56] References Cited

U.S. PATENT DOCUMENTS 4,031,885  6/1977  Davis et al. ........................ 128/720
4,197,859  4/1980  Prestele .............................. 128/720

FOREIGN PATENT DOCUMENTS 1111732  9/1984  U.S.S.R. ............................ 128/720

OTHER PUBLICATIONS

Finucane et al.; "Estim. of Alveolar Press. During Forced Oscillation of Resp. System"; Journal of Applied Phys., vol. 38, No. 3, Mar. 1975, pp. 531–537.
Goldman et al.; "Simplified Measurement of Resp. Resistance by Forced Oscillation"; J. of Applied Phys.; vol. 28, No. 1, Jan. 1970, pp. 113–116.
Pimmel et al.; "Instrumentation for Measuring Resp. Impedance by Forced Oscillations"; IEEE Trans. on Biomed. Engr., vol. BME-24, No. 2; Mar. 1977; pp. 89–93.
Lenney et al.; "Measurement of Total Resp. Resist. in Pre-School Children Using a Modif. of the Forced Oscill. Technique"; J. of Med. Engr. and Techn.; vol. 2, No. 4, Jul. 1978, pp. 190–193.

Primary Examiner—Angela D. Sykes
Attorney, Agent, or Firm—Baker & Botts

[57] ABSTRACT

An infant respiratory impedance measuring apparatus and method using forced oscillations is disclosed. In order to account for the effects of the mask, a shunt compliance is placed in parallel with the components representing the impedance of the infant.

11 Claims, 2 Drawing Sheets

INFANT RESPIRATORY IMPEDANCE MEASURING APPARATUS AND METHODS USING FORCED OSCILLATIONS

FIELD OF THE INVENTION

The invention relates to an infant respiratory impedance measuring apparatus and method using forced oscillations.

BACKGROUND OF THE INVENTION

Traditional pulmonary function tests such as spirometry, require patient cooperation and thus are generally inappropriate for infants and are often ineffective for young children. The forced oscillation technique, introduced by Dubois et al. (1956), has been used on healthy adults, as well as adults with respiratory disease, to obtain respiratory impedance data over various frequency ranges. Respiratory impedance ($Z_{in}$) is defined as the complex ratio $$Z_{in} = \frac{P_{ao}}{\dot{V}_{ao}}$$

where $P_{ao}$ and $\dot{V}_{ao}$ are the pressure and flow, respectively, at an airway opening. $Z_{in}$ is often expressed by its real and imaginary components versus frequency (i.e. an impedance spectrum). Presumably, the $Z_{in}$ spectrum reflects the mechanical properties of the respiratory system. Consequently, mechanical models have been used to interpret adult human $Z_{in}$ data. For example, healthy $Z_{in}$ over the frequency range of 2 to 32 Hz allows the estimation of total respiratory system resistance, inertance and compliance by analysis using a three-element model consisting of a resistance, inertance and a compliance in series. For patients with respiratory disease, these properties can change accordingly. Often, the spectral shape itself changes as well, motivating additional model properties and model structure. For example, in adult human subjects, the $Z_{in}$ data from 5 to 320 Hz includes an airway acoustic anti-resonance which may permit noninvasive insight on airways alone as proposed by Jackson et al (1989). In smaller mammals such as dogs, both tissue specific and airway specific antiresonances were identified in the $Z_{in}$ data between 2 and 256 Hz (Jackson and Lutchen, 1991). In the past, a six-element model (FIG. 1) has also been used to describe $Z_{in}$. The components of the six-element model are divided into airway parameters ($R_{aw}$, $I_{aw}$) and tissue parameters ($R_t$, $I_t$, $C_t$) which are separated by a shunt compliance ($C_g$) representing gas compressibility. However, normal infant $Z_{in}$ data for frequencies of 256 Hz or less may not justify a model of this complexity.

Because the forced oscillation technique is noninvasive and relatively simple, it can be applied to infants. Using the forced oscillation technique, $Z_{in}$ measurements can be quickly made during quiet breathing with minimal discomfort to the infant. Few studies have reported measurements in non-intubated infants using the forced oscillation technique (See, for example, Desager et al., 1991; Marchal et al., 1989; Hordvik et al., 1985; Nussbaum and Galant, 1984; Wohl et al., 1969). However, these measurements were typically constrained to low frequencies (e.g., $f<40$ Hz). Also, unlike adult $Z_{in}$ data, these data required that a mask be placed over the infants oral and nasal cavities and that the oscillations be presented through the nose. As a consequence, it remains heretofore unresolved as to how the mask and specific physiologic properties contribute to the $Z_{in}$ spectrum.

While various models have been used in the prior art, none have specifically taken into account the effect of the mask on the $Z_{in}$ data. This is obviously a drawback which may lead to erroneous results.

SUMMARY OF THE INVENTION

It is an object of the present invention to overcome these and other drawbacks of the prior art.

It is a further object of the present invention to provide a method and apparatus for measuring infant respiratory impedance using forced oscillations.

It is another object of the present invention to provide a model to accomplish the foregoing.

In order to accomplish these and other objects of the invention, there is provided an apparatus and method for measuring the respiratory impedance of infants using forced oscillations, wherein the apparatus comprises a computer for generating a pseudo-random noise signal which is provided to a power amplifier, then to a loudspeaker plethysmograph, to flow and pressure measuring devices which produce first and second outputs which are applied to an amplifier and low pass filter and then to a computer. The $Z_{in}$ is calculated by dividing the pressure by the flow and this information may be applied to a model to obtain information about the infants respiratory system.

According to one embodiment of the invention, a four-element model is used and comprises an input node and a first branch connected to the input node comprising a capacitive element having a value $C_m$ corresponding to characteristics of a mask placed over the infant's nose and mouth, and a second branch connected to the input node comprising an impedance having characteristics corresponding to a respiratory system including, for example, a resistance $R_{rs}$, an inductance $I_{rs}$ and a capacitance $C_{rs}$ connected in series and having values corresponding to mechanical characteristics of the infant's respiratory system.

DETAILED DESCRIPTION OF THE PREFERRED EMBODIMENTS

Figure 3:
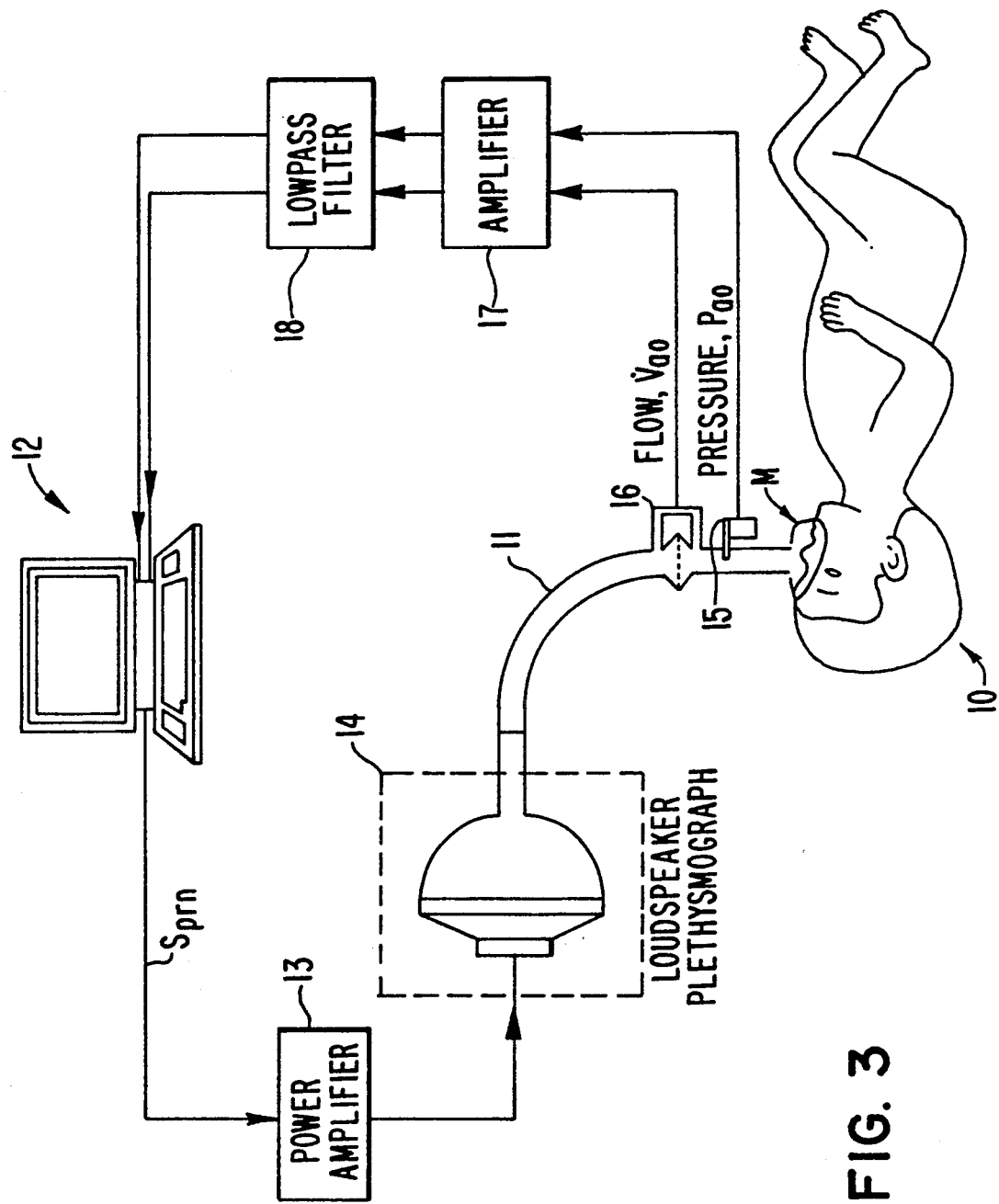
FIG. 3 is a schematic illustration of a infant respiratory impedance measuring system according to one embodiment of the present invention.

According to one embodiment of the present invention, and with reference to FIG. 3, for example, there is provided an apparatus and method for measuring respiratory impedance in infants using a forced oscillation technique. As shown in FIG. 3, there is an infant 10 with a mask M located over its nose and mouth.

A pseudo-random noise signal having a frequency f is generated by a digital computer 12 (e.g., a DEC 11/73), and is translated through a digital-to-analog converter (not shown), amplified by a lower amplifier 13 and used to drive a loudspeaker plethysmograph 14. Preferably, $4<f<256$ Hz, but higher frequencies may also be desired. The loudspeaker 14 is preferably mounted in a semi-spherical chamber with orifices for bias flow to provide fresh air and for attaching to the infant. The mask is connected to the loudspeaker plethysmograph 14 via a flexible tube 11 (e.g., a tube having a length of 60 cm and a diameter of 3.2 cm) or another suitable connecting device. Pressure at the airway opening ($P_{ao}$) is measured with a transducer 15 in a known manner (for example, with a Model 163PC by Microswitch). A second transducer 16 is used to measure flow ($\dot{V}_{ao}$) at the airway opening in a known manner (for example, with a pneumotachometer and a Celesco LCVR pressure transducer). Preferably, the flow is calculated by measuring the pressure drop across a pneumotachometer (e.g., an XX cm diameter capillary). To reduce the noise level so that the infant is not disturbed, the loudspeaker flow generator may be completely contained in a baffle box.

In operation, the speaker is driven by the computer generated pseudo-random signal. For example, the signal may vary from 4–256 Hz in 4 Hz increments. A standard infant face mask (for example, one of the type available from Vital Signs, Inc.) is held firmly over the infant's nose and mouth. The mask is used to connect the generator and sensors to the infant. The pressure $P_{ao}$ and flow $\dot{V}_{ao}$ signals amplified by amplifier 17 are passed through a low-pass filter 18 having a cutoff frequency of, for example, 256 Hz and returned to the computer 12 via an analog-to-digital converter (not shown) for computations.

Preferably, during measurement, the infant is placed supine with its neck slightly extended. Quiet sleep is preferred before the data collection begins. The face mask is placed over the mouth and nose of the infant and a plurality (e.g. eight) sequential bursts of random noise are generated, resulting in $Z_{in}$ data acquisition. Each burst of data is automatically triggered during the inspiration portion of the breathing cycle. If the infant moves or wakes up, the mask is removed and the infant is given time to go back to sleep. A plurality of sets (e.g. 24) of $Z_{in}$ data may be acquired for each infant. Of these, a number may be chosen as the most reproducible and least noisy and may be ensemble averaged and the coherence calculated (in a known manner). If the coherence is less than 0.8 at any given frequency, then the $Z_{in}$ data point at that frequency may be discarded.

After $Z_{in}$ is calculated by taking the ratio of pressure $P_{ao}$ and flow $V_{ao}$ at the airway opening, the $Z_{in}$ data is analyzed using lumped-element electromechanical models. Analysis in this general manner is known. The parameters in these models are estimated by fitting the data using a standard nonlinear gradient-based technique to minimize the performance index, $p_i$ where:

$$p_i = \frac{\sum_{i=1}^{n} |Z_{rs,d}(f_i) - Z_{rs,m}(f_i)|^2}{|Z_{rs,d}(f_i)|^2} \quad (2)$$

where
n = the number of data points,
$f_i$ = frequency,
$Z_{in,d}(f_i)$ = actual $Z_{in}$ data at frequency $f_i$ and
$Z_{in,m}(f_i)$ = model predicted $Z_{in}$ data at frequency $f_i$.
The measure of goodness of fit to the model is represented by $\sigma^2$ where $$\sigma^2 = \frac{p_i}{n - p} \quad (3)$$

$$\sigma^2 = \frac{p_i}{n - p} \quad (3)$$

The $\sigma^2$ reflects the goodness of fit and is also used to calculate the confidence bounds on the model parameters.

EXAMPLE

A study was conducted in 9 infants (4 to 28 months) with no history of chronic or acute lung disease. The physical characteristics of the infants are shown in Table 1.

TABLE 1

| | Physical characteristics of infants. | | | |
|---|---|---|---|---|
| INFANT | SEX | AGE (MONTHS) | LENGTH (CM) | WEIGHT (KG) |
| EM | MALE | 4.0 | 62.0 | 5.5 |
| EC | FEMALE | 6.0 | 70.0 | 8.6 |
| AM | MALE | 7.0 | 70.0 | 7.5 |
| TC | FEMALE | 8.0 | 70.0 | 8.0 |
| MFM | MALE | 8.0 | 63.0 | 5.5 |
| DFB | MALE | 8.5 | 72.0 | 8.0 |
| SM | FEMALE | 14.0 | 80.0 | 10.4 |
| AS | FEMALE | 16.0 | 78.7 | 9.0 |
| KT | FEMALE | 28.0 | 87.5 | 15.0 |
| MEAN ± S.D. | | 11.1 ± 7.0 | 72.6 ± 7.7 | 8.6 ± 2.7 |

The infants were being evaluated for non-respiratory medical symptoms. The clinical procedures used (magnetic resonance, CNS imaging, or echocardiogram) required that the infants be sedated with chloral hydrate (50–100 mg/kg). Following these procedures, measurements of $Z_{rs}$ were taken while the infant was recovering from sedation.

Figure 1:
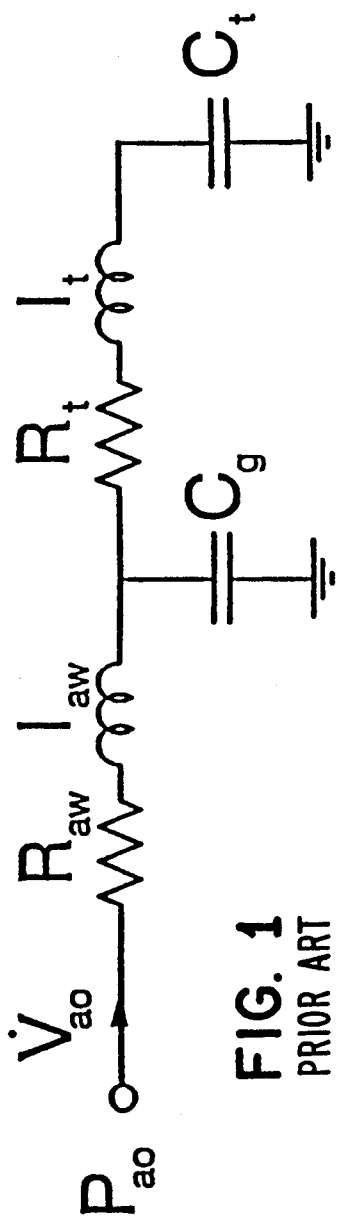
FIG. 1 is a schematic diagram of a six-element model used in the prior art.
Figure 2:
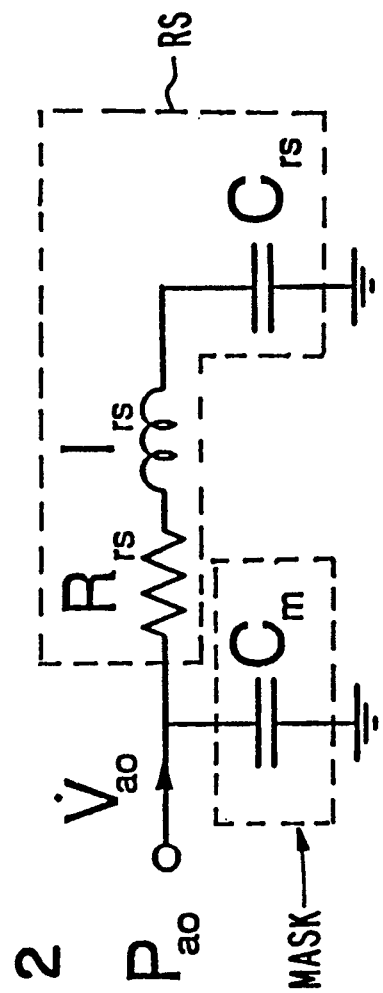
FIG. 2 is a schematic diagram of a four-element model which may be used in connection with the present invention.

Since $P_{ao}$ is sampled between the mask and the pneumotachometer, the impedance of the mask is included in the infant $Z_{in}$ measurements. Since the mask is a simple rigid structure containing a volume of compressible gas, according to one aspect of the present invention, it is modelled as a shunt compliance ($C_m$) in parallel with the infant. Preferably, the $C_m$ represents the gas compression due to the volume of gas in the face mask during the $Z_{in}$ measurements. In this model, the anti-resonant peak in the real part of the $Z_{in}$ data is due in part to the $C_m$ resonating with the inertance of the respiratory system $I_{rs}$. According to this aspect of the invention, it is preferable to fit the normal infant $Z_{in}$ data (between 4 and 256 Hz) with a four-element model (FIG. 2) which includes a series combination of three infant respiratory parameters ($R_{rs}$, $L_{rs}$, $C_{rs}$) collectively referred to as $Z_{rs}$ connected in parallel with a shunt compliance ($C_m$), representing the volume of gas in the mask. These four parameters are estimated using the procedures presented with Examples 2 and 3 set forth below. The four-element model provides a good visual and statistically unique fit to the data and provides the statistically well-defined parameter values given for example in Table 2.

TABLE 2

| | Parameter estimates for four-element model. | | | | |
|---|---|---|---|---|---|
| INFANT | $C_m$ ml/ cmH$_2$O | $R_{rs}$ cmH$_2$O/ L/s | $I_{rs}$ cmH$_2$O/ L/s$^2$ | $C_{rs}$ ml/ cmH$_2$O | $\sigma^2$ |
| EM | 0.040 | 19.7 | 0.023 | 1.39 | 0.011 |
| EC | 0.049 | 18.9 | 0.028 | 0.62 | 0.013 |
| AM | 0.043 | 19.0 | 0.025 | 4.67 | 0.031 |
| TC | 0.040 | 22.3 | 0.030 | 1.26 | 0.001 |

TABLE 2-continued

Parameter estimates for four-element model.

| INFANT | $C_m$ ml/ cmH$_2$O | $R_{rs}$ cmH$_2$O/ L/s | $I_{rs}$ cmH$_2$O/ L/s$^2$ | $C_{rs}$ ml/ cmH$_2$O | $o^2$ |
|---|---|---|---|---|---|
| MFM | 0.042 | 19.5 | 0.026 | 0.85 | 0.012 |
| DFB | 0.039 | 19.5 | 0.034 | 1.22 | 0.017 |
| SM | 0.043 | 17.0 | 0.025 | 1.84 | 0.005 |
| AS | 0.033 | 26.4 | 0.038 | 1.58 | 0.005 |
| KT | 0.070 | 11.6 | 0.019 | 2.34 | 0.025 |
| MEAN ± S.D. | 0.044 ± 0.010 | 19.3 ± 3.7 | 0.028 ± 0.005 | 1.75 ± 1.14 | 0.013 ± 0.0009 |

The $C_m$ varied from 0.033 to 0.070 ml/cmH$_2$O which would result from 32 to 47 ml of air in the mask. Since the volume of gas that would be contained in the empty mask alone is 50 ml, the estimated $C_m$ values were within the acceptable range. The $R_{rs}$ values varied from 11.6 to 26.4 cmH$_2$O/L/s (with a mean of 19.3±3.7 cmH$_2$O/L/s). The oldest (28 months) and largest (15.0 kg) infant, "KT," had a significantly smaller $R_{rs}$ (11.6 cmH$_2$O/L/s) than the remaining infants, as expected. The $I_{rs}$ values were very closely clustered among the infant population, with the mean $I_{rs}$ equal to 0.028±0.005 cmH$_2$O/L/s$^2$. Finally, the $C_{rs}$ values varied from 0.62 to 2.34 ml/cmH$_2$O (with a mean of 1.75±1.14 ml/cmH$_2$O).

Therefore, according to one aspect of the invention, $Z_{in}$ data over the frequency range of 4 to 256 Hz may be obtained from infants with healthy respiratory systems and a mechanical model may be used to estimate specific mechanical properties of the infants respiratory system. However, the $Z_{in}$ data can be acquired beyond 256 Hz. This may increase the number of distinct mechanical properties available, but it would not obviate the need to compensate for the face mask in a manner similar to the four-element model. Conversely, reducing the frequency range by taking data below 256 Hz may jeopardize the ability to remove the influence of the face mask. Finally, from this information, a determination may be made as to how the mechanical parameters would change as a function of infant size and age.

To further test the appropriateness of the four-element model, a simple experiment was designed. $Z_{in}$ data were collected from one of the infants as described above. Immediately following the $Z_{in}$ measurements, the dead space in the mask was altered. A sticky, resilient putty sold under the trademark (PLAY-DOH) was carefully inserted around the internal surfaces of the face mask to decrease the dead space without affecting the breathing of the infant. $Z_{in}$ measurements were then repeated. After the experiment, the sticky, resilient putty sold under the trademark (PLAY-DOH) was removed and the volume of the Play-doh ® was measured to be approximately 12 ml. Both sets of $Z_{in}$ data were analyzed using the four-element model and the results are shown in Table 3.

TABLE 3

Comparison of four-element model parameters for infant EM with normal face mask and face mask with dead space.

| INFANT | $C_m$ ml/cmH$_2$O | $R_{rs}$ cmH$_2$O/ L/s | $I_{rs}$ cmH$_2$O/ L/s$^2$ | $C_{rs}$ ml/cmH$_2$O | $o^2$ |
|---|---|---|---|---|---|
| EM (normal face mask) | 0.040 | 19.6 | 0.023 | 1.39 | 0.011 |
| EM reduced dead space | 0.030 | 23.1 | 0.029 | 1.96 | 0.017 |

The differences between the $R_{rs}$, $I_{rs}$ and $C_{rs}$ are relatively small, whereas the $C_m$ decreased from 0.040 ml/cmH$_2$O to 0.030 ml/cmH$_2$O correlating with a decrease of volume of about 10 ml. Thus, the four-element model accurately captured the physical decrease in dead space in the mask with a corresponding decrease in the $C_m$ estimates. Thus, using a four-element model, physiologic parameter estimates of resistance, compliance and inertance of the infant respiratory system may be found. While the use of the four element model is particularly useful for frequencies up to 256 Hz, it may also be used at higher frequencies. However, it may also be desirable to use the four element model for frequencies up to 256 Hz and use another type (e.g., a six element) model, for frequencies above 256 Hz. When used with diseased infants, a model may include one or more elements to account for the increased complexity of the system due to the disease.

The foregoing is a description of the preferred embodiments of the present invention. Various modifications will be readily apparent to one of ordinary skill in the art. The invention is only limited by the claims appended hereto.

We claim:

1. A four-element model for use in an infant respiratory impedance measuring system, wherein a mask is placed over an infant's face, said model comprising:
   a node;
   an impedance connected to said node, wherein said impedance corresponds to the respiratory impedance of an infant and comprises three of said four elements; and
   a shunt compliance connected to said node in parallel with said impedance, where the shunt compliance corresponds to characteristics of said mask and comprises a fourth of four elements.

2. The model of claim 1 wherein said impedance comprises a resistance comprising a first of said four elements, a compliance comprising a second of said four elements, and an inertance comprising a third of said four elements and wherein said resistance, compliance and inertance correspond to the respiratory system of said infant.

3. A respiratory impedance measuring system comprising:
   a mask which is located over the face of a subject;
   means for measuring a pressure and a flow at an airway opening of said subject;
   means for dividing said pressure by said flow to determine a respiratory impedance of said subject; and
   means for analyzing said respiratory impedance using a model comprising:
   an impedance element corresponding to the respiratory impedance of said subject; and
   a shunt compliance connected in parallel with said impedance element, where the shunt compliance corresponds to characteristics of said mask.

4. The system of claim 3 wherein said impedance element comprises a resistance, an inertance, and a compliance connected in series with each other.

5. A method of measuring respiratory impedance comprising:
   placing a mask over a subject's face;
   measuring a pressure and a flow at an airway opening of the subject;
   dividing said pressure by said flow to determine a respiratory impedance;
   applying said respiratory impedance to a model comprising:
   a node;
   an impedance connected to the node, wherein said impedance corresponds to the respiratory impedance of the subject; and
   a shunt compliance connected to said node in parallel with said impedance, wherein the shunt compliance corresponds to characteristics of said mask.

6. The method of claim 5 further comprising the steps of generating a signal having a predetermined frequency and applying said signal to said subject.

7. The method of claim 5 further comprising the steps of generating a signal having a frequency of up to 256 Hz and applying said signal to said subject.

8. The method of claim 5 further comprising the steps of generating a signal having a frequency of greater than 256 Hz and applying said signal to said subject.

9. The method of claim 5 further comprising the steps of generating a plurality of signals having predetermined frequencies and applying said signals to said subject.

10. The method of claim 5 further comprising the steps of generating a plurality of signals having each having a frequency of up to 256 Hz and applying said signals to said subject.

11. The method of claim 5 further comprising the steps of generating a plurality of signals at least one of which has a frequency greater than 256 Hz and applying said signals to said subject.

* * * * *